United States Patent [19]
Shieh

[11] Patent Number: 6,156,017
[45] Date of Patent: Dec. 5, 2000

[54] CLEANING DEVICE

[76] Inventor: Shin Jiu Shieh, 2nd Fl., No. 7, Alley 5, Lane 94, Yung Li Rd., Yung Ho City, Taipei Hsien, Taiwan

[21] Appl. No.: 09/132,242

[22] Filed: Aug. 11, 1998

[51] Int. Cl.[7] .................................................. A61M 31/00
[52] U.S. Cl. .......................... 604/279; 604/275; 604/19; 604/48; 604/118; 604/257
[58] Field of Search ................ 604/275, 19, 48, 604/515, 73, 93, 95, 104, 118, 181, 246, 257, 279, 93.01, 95.01

[56] References Cited

U.S. PATENT DOCUMENTS

| | | | |
|---|---|---|---|
| 2,117,622 | 5/1938 | Morton et al. ........................... | 128/251 |
| 2,199,844 | 5/1940 | Tucker .................................... | 128/251 |
| 3,769,976 | 11/1973 | Victory ................................... | 128/229 |
| 4,601,709 | 7/1986 | Kabbaby ................................. | 604/150 |
| 4,680,026 | 7/1987 | Weightman et al. ..................... | 604/33 |
| 4,850,965 | 7/1989 | Zinopoulos et al. ..................... | 604/73 |
| 4,894,053 | 1/1990 | Reddick .................................. | 604/85 |
| 4,911,704 | 3/1990 | Dixon ..................................... | 604/83 |
| 4,950,231 | 8/1990 | Liu .......................................... | 604/39 |
| 5,267,981 | 12/1993 | Ducoin et al. .......................... | 604/275 |
| 5,304,116 | 4/1994 | Cornelius ................................ | 604/39 |
| 5,348,555 | 9/1994 | Zinnanti ................................. | 606/49 |
| 5,419,772 | 5/1995 | Teitz et al. .............................. | 604/141 |
| 5,447,494 | 9/1995 | Dorsey, III ............................. | 604/43 |
| 5,830,214 | 11/1998 | Flom et al. ............................. | 606/41 |
| 5,921,970 | 7/1999 | Vandenberg ............................ | 604/264 |
| 5,971,956 | 10/1999 | Epstein .................................. | 604/119 |

Primary Examiner—Corrine McDermott
Assistant Examiner—Chris L. Rodriguez
Attorney, Agent, or Firm—Rosenberg, Klein & Lee

[57] ABSTRACT

A cleaning device is a device directly connected with a bath shower head. It is primary used in the individual hygiene. The structure thereof includes a joint directly connected a general used shower bath device. The body of the cleaning device connected with the joint is made by resin and has a cylindrical holding portion matching the requirement of ergonomics. A water box and a cleaning channel are formed within the holding portion. A rotary nozzle is connected on another end of the holding portion, which may be inserted into an organization (for example excretory organs) for cleaning. The present invention may be directly used in shower bath devices of any bathroom.

4 Claims, 6 Drawing Sheets

CLEANING DEVICE

BACKGROUND OF THE INVENTION

The present invention relates to a cleaning device matching the requirement of the individual hygiene. Since a cleaning device of the present invention has a joint that may be directly connected the shower head of the bath room, a water outlet button freely controlled, and a rotary nozzle, thus it may satisfy the individual requirement by any way in any place.

The current used individual cleaning devices are generally made by ceramics. It has a water storing can, a water pump, and other components, preferably, a temperature control device may be further installed. Thus the structure thereof is large and expensive. Therefore, it is not suitable as a home using device.

Another, a commercial container is generally used in the department of gynaecology and obstetrics, which is similar a beer bottle in which disinfect water or warm water is filled so that the bottle mouth may be inserted into the organ for cleaning. The defect of this prior art device is that water is sprayed by pinching, thus the spraying range is small. If the using period is too long, the water temperature will decrease, thus it is not suitable to be used in winter. The cleanness of the bottle mouth is also a question.

The cleaning device of individual organ is very important, especially in confinement after giving birth a children. During that time, women are needed to clean vagina everyday. But aforementioned bottle type device is inconvenient and uncomfortable.

The present invention has improved above defects. At first, the convenience is considered, thus a cleaning device may be combined with a general used shower bath device is designed. The cleaning device has a cylindrical smooth holding portion, which is combined with a rotary nozzle with rotation angle between 0 to 45 degrees. Thus the temperature of shower bath water may suit the human body by properly adjusting.

BRIEF DESCRIPTION OF THE DRAWINGS

The present invention will be better understood and its numerous objects and advantages will become apparent to those skilled in the art by referencing to the following drawings in which.

DESCRIPTION OF THE PREFERRED EMBODIMENT

Figure 1:
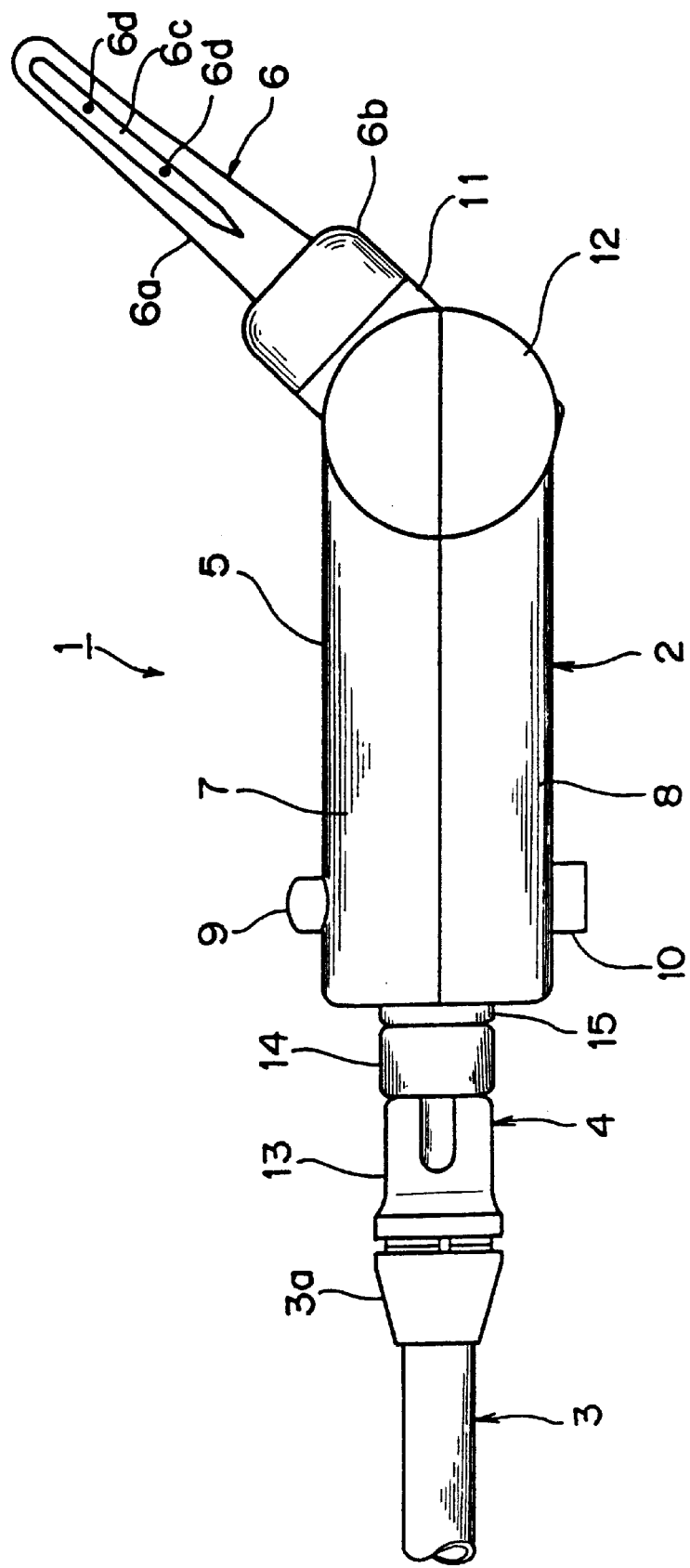
FIG. 1 is a front view of the present invention.

Referring now to FIG. 1, the cleaning device (1) comprises a body (2) formed by a holding portion (5). The holding portion (5) includes an upper portion (7) and a lower portion (8) which are formed by an upper semi-cylinder and a lower semi-cylinder, respectively. This holding portion has a smooth shape matched the requirement of ergonomics. One side thereof is directly screwedly connected with the soft tube of a shower head by a joint (4). Another end of the holding portion (5) is a nozzle (6) for being inserted into an organization.

Figure 2:
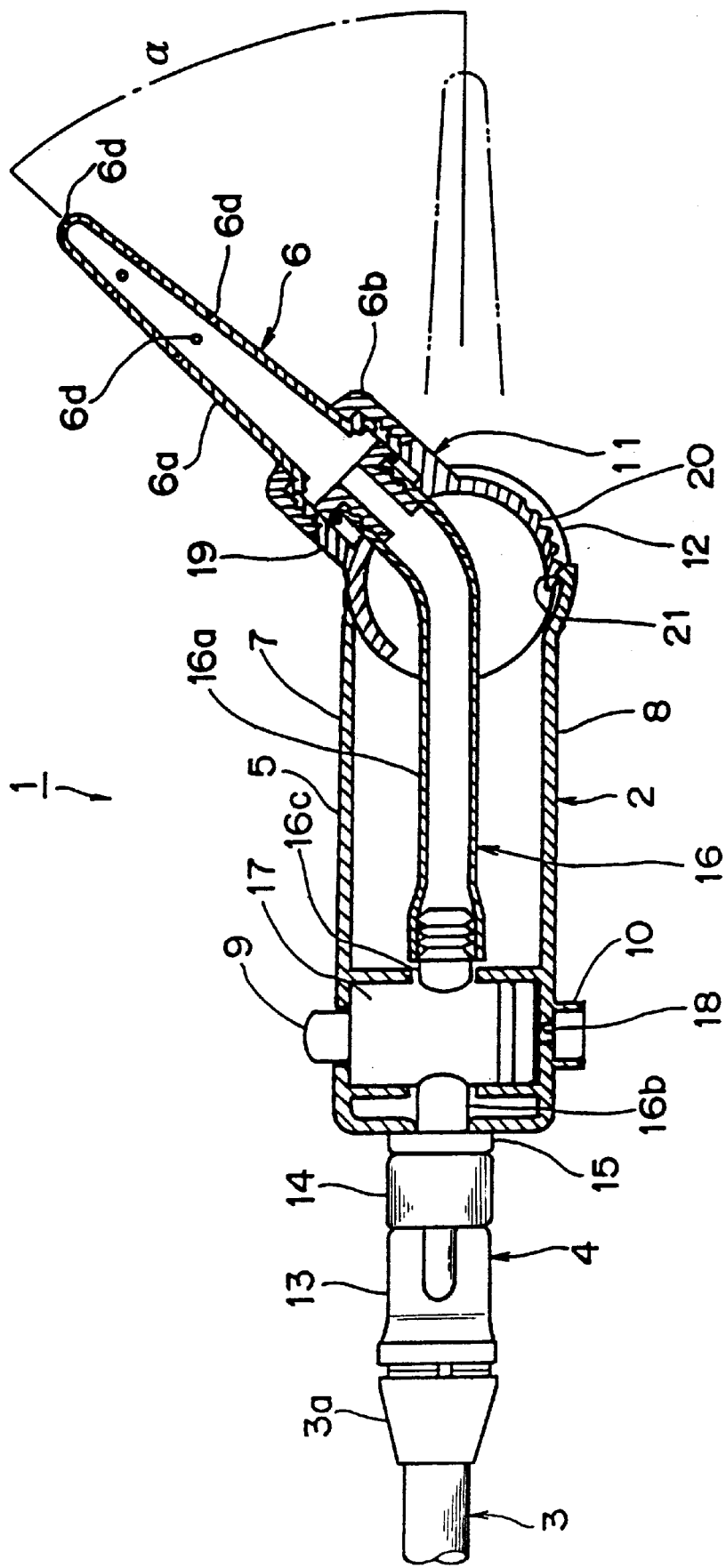
FIG. 2 is a partial cross sectional view of the present invention.

Referring now to FIG. 2, the structure of the holding portion is disclosed. A button is installed on the rear end of the upper side of the upper portion (7), and a plastic water drain tube (10) is installed on the lower half (8) with respect thereto. Another end of the holding portion (5) is a joint portion (11) which may be screwedly connected with the nozzle (6).

Nozzle (6) has a smooth surface made by synthetic resin, the medium portion of which has a rod shape structure (6a), and the lower portion of which has a screwed structure (6c) which may be screwedly inserted into the joint portion (11). A polarity of water outlets (6d) are installed on the proper positions of the nozzle (6) so that the cleaning liquid may flow out successfully.

Figure 4:
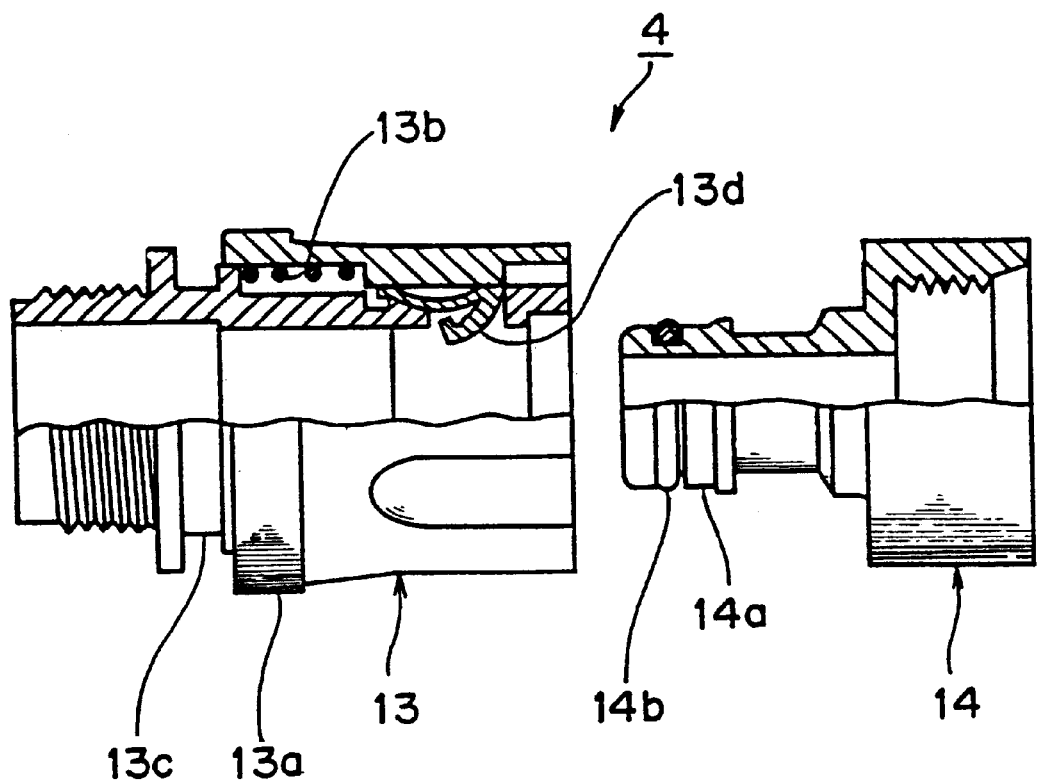
FIG. 4 is an exploded view of the present invention.

As shown in FIG. 4, the joint (4) is divided into a female element (13) and a male element (14). These two portions are connected by the soft tube joint (3) of the shower head. An elastic pad (13b) and a braking block are installed on the inner portion of the front end tube (13a) of the male element (13). A tightly sealed screwed portion (14b) for waterproof is installed outside the protrude portion (14a) on the front end of the male element (14). In engagement, the male element (14) is screwed into the female element (13) and now the braking block (13d) will buckle the two elements so not to separate with each other. If it is required to separate the two elements, it is only needed to push the braking block (13d) so that the braking block (13d) will leave the buckling position, and the two elements are separated.

Figure 3:
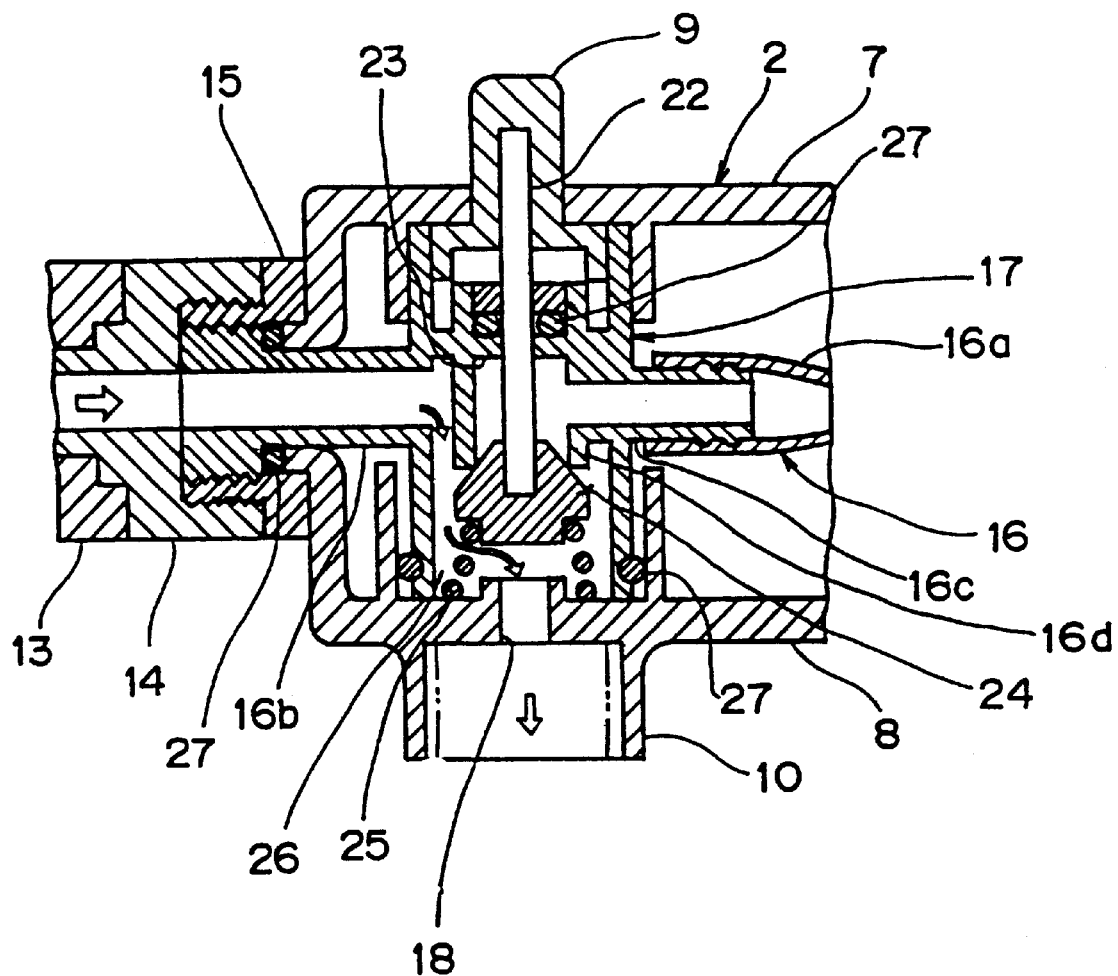
FIG. 3 is an enlarged view of the inner structure of holding portion.

As shown in FIGS. 2, 3 and 4, a water box (17) of the holding portion (5) connected with the plastic soft tube is located between the plug (15) of the connecting means and the joint (4). The water box (17) is communicated with the cleaning channel (16) of the nozzle (6), wherein the flowing of water therebetween is controlled by a button (9).

A side plate is installed on the joint end (11) for supporting the structure of the holding portion (5). A teeth structure (20) is installed on the proper position of the lower end near the nozzle (6) of the lower portion (8) so that the holding portion (5) and the nozzle (6) may engage with each other during connecting, and the nozzle may rotate with an angle of 0 degrees to 45 degrees, while in each angle, the nozzle (6) may fixedly rotate.

As shown in FIG. 3, the water box (17) is protruded from the plug (15) on the rear end of the body (2), fixed on the water channel (16b), and embedded into the cleaning channel (16) of the soft plastic tube (16). The front end of the water channel (16) is extended outwards. As shown in the figure, the button (9) is extended with a long rod (22) and then passed through a spacer (23) to fix a plunger member (24) on the lower end of the box (17). A spring is installed between the plunger member (24) and the lower portion (8) and is adhered at the upper end to the plunger member (24). Thus as the button (9) has not be pushed, the combining barrel (16d) at the lower water channel of box (17) is closed by plunger member (24). Thus, the cleaning water will flow into the water box (17) from the upper channel (16) on the upper stream. In the water channel (16), the cleaning water may flow out from the screw hole (27) between the long rod (22) and the water box (17).

Figure 5:
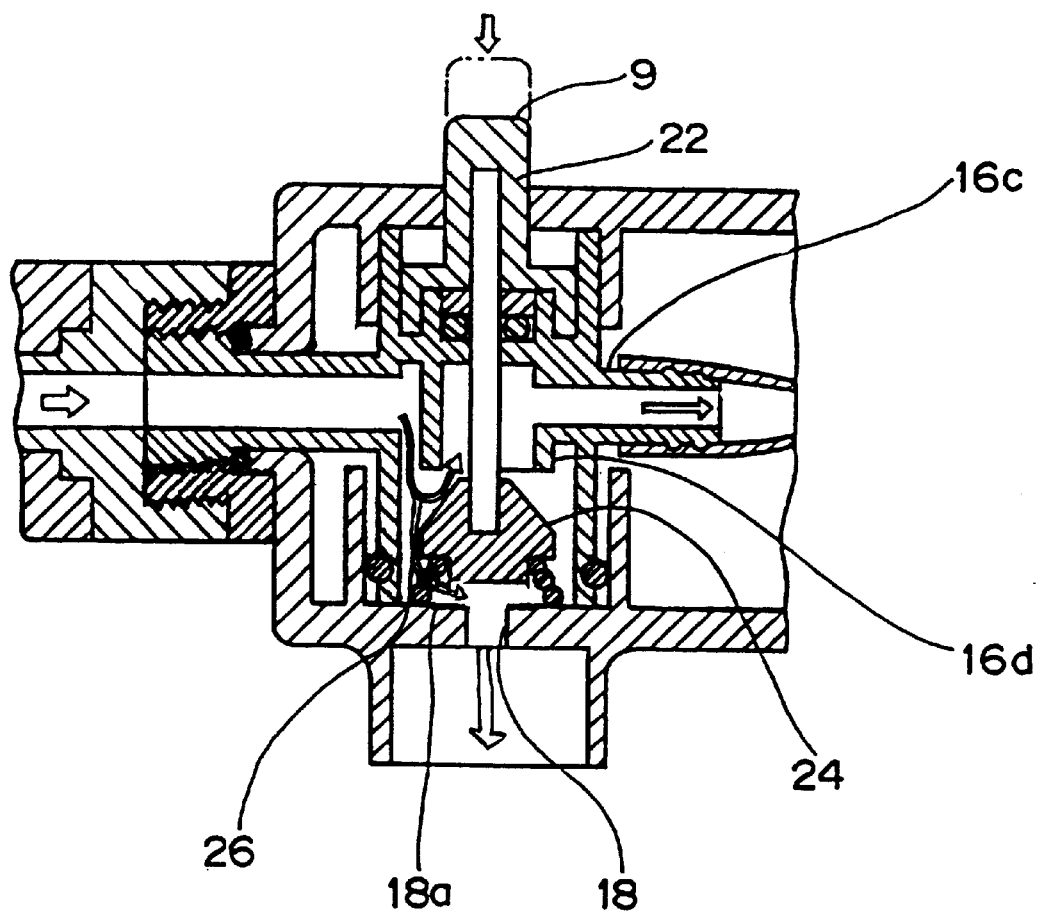
FIG. 5 is a schematic view shown the operation of the present inventionm

As shown that in FIG. 5, as the button (9) is pushed, the box (24) will separate with the combining barrel (16d), now the water will flow to the side channel (16c) from another opening (26). When the button (9) is pushed to the lowest position, the lower portion of the plunger member (24) will contact with the ring structure (18a) within the water outlet (18), thus the water flow of cleaning water may be adjusted.

Figure 6A:
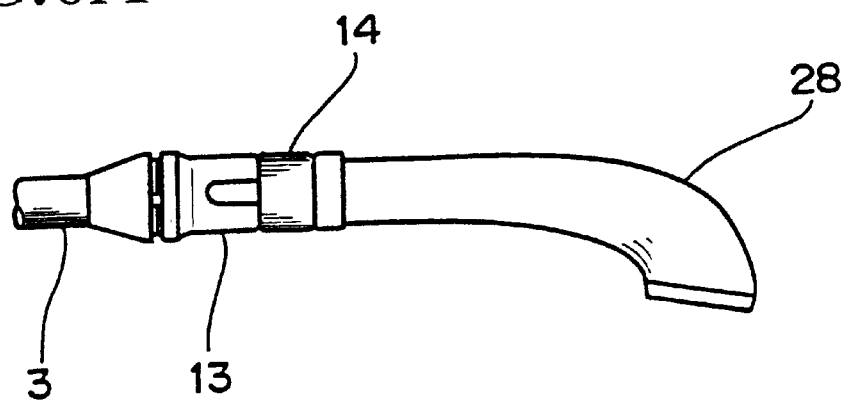
FIG. 6A is a schematic view of a water outlet end detachably coupled to a female element of a tube joint; and, FIG. 6B is a schematic view illustrating the detachable coupling of components to a female element of a tube joint in accordance with a embodiment of the present invention.
Figure 6B:
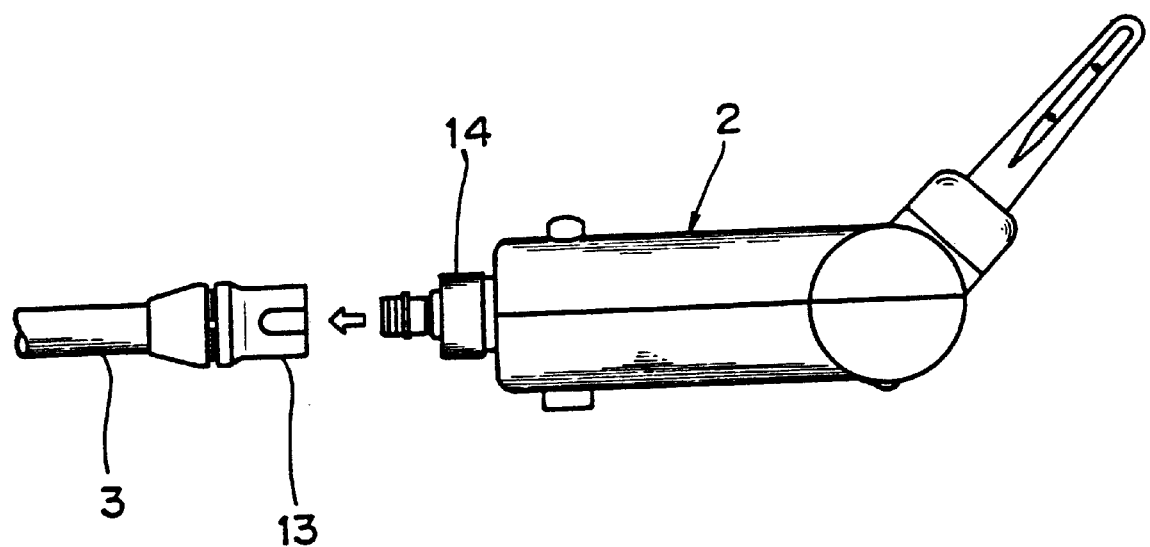

The general used shower head is shown in FIG. 6, the water outlet end (28) may be detached from the combined male element (14). Then the male component of the present invention may be installed, thus it may be combined successfully with the shower head. Since most of the shower bath devices have fix sizes, thus the male and female elements of the present invention are designed with the same sizes, therefore, the usage of the present invention is widely.

After combining, the nozzle (6) is inserted into organization, and the water flow is controlled by button (9), thus the user may use this device easily. Those skilled in the art will readily recognize various modifications and changes which may be made to the present invention without strictly following the exemplary embodiment and application illustrated and described herein, and without departing from the true spirit and scope of the present invention which is set forth in the following claims.

What is claimed is:

1. A cleansing device for controlling the delivery of a fluid comprising:

(a) a joint portion adapted for coupling to a fluid supply outlet, said joint portion having:

(1) coaxially coupled male and female elements, said male element having formed thereon axially offset screw and protrusion portions; and, (2) means for detachably securing said coupling of said male and female elements, said means including an elastic pad and a braking block retained within said female element for respectively engaging said screw and protrusion portions of said male element;

(b) a holding portion coupled to said joint portion for receiving and adjustably directing the fluid therethrough, said holding portion having a distal end; and, (c) a nozzle portion coupled to said distal end of said holding portion, said nozzle portion having formed therein a plurality of water outlets for discharging the fluid received from said holding portion, said nozzle portion being configured for engagement with the area being cleansed.

2. The cleansing device as recited in claim 1 wherein said holding portion includes adjustment means for adjustably controlling the flow of fluid therethrough, said adjustment means including a control button and a plunger member coupled thereto by an elongate rod, said plunger member being displaceable upon actuation of said control button to responsively impede the flow of fluid.

3. The cleansing device as recited in claim 1 wherein said nozzle portion is coupled in angularly adjustable manner to said holding portion.

4. The cleansing device as recited in claim 3 wherein said nozzle portion includes a nozzle end threadedly coupled to a joint end, said joint end engaging said distal end of said holding portion in said angularly adjustable manner.

* * * * *